(12) United States Patent
Perkins et al.

(10) Patent No.: US 6,349,725 B1
(45) Date of Patent: Feb. 26, 2002

(54) ANESTHESIA MASK FOR ANIMALS

(75) Inventors: D. H. Perkins, Woods Cross; Ray H. Perkins; Ryan C. Perkins, both of Bountiful, all of UT (US)

(73) Assignee: Genesis Medical Technologies, LLC, Bountiful, UT (US)

( * ) Notice: Subject to any disclaimer, the term of this patent is extended or adjusted under 35 U.S.C. 154(b) by 0 days.

(21) Appl. No.: 09/468,979

(22) Filed: Dec. 21, 1999

(51) Int. Cl.$^7$ ............................................... A62B 18/02
(52) U.S. Cl. ............................. 128/206.21; 128/206.24
(58) Field of Search ..................... 128/206.21–206.24, 128/206.26–206.28, 200.24, 200.28, 205.25, 205.26, 203.12, 203.29, 205.19, 203.15, 203.21, 201.22, 201.23; 119/450

(56) References Cited

U.S. PATENT DOCUMENTS

| | | | | |
|---|---|---|---|---|
| 1,812,380 A | * | 6/1931 | Stelzner | 128/205.26 |
| 1,840,957 A | * | 1/1932 | Kaehler | 128/205.26 |
| 2,312,714 A | | 3/1943 | Herbin | 128/141 |
| 2,811,966 A | * | 11/1957 | Hull | 128/205.26 |
| 2,843,119 A | * | 7/1958 | Glasser | 128/142 |
| 3,505,998 A | | 4/1970 | Halstead et al. | 128/146.7 |
| 4,002,167 A | | 1/1977 | Rambosek | 128/205 |
| 4,332,244 A | * | 6/1982 | Levy et al. | 128/205.25 |
| 4,513,741 A | * | 4/1985 | Demi | 128/205.25 |
| 4,546,768 A | * | 10/1985 | Ferierabend | 128/200.16 |
| 4,577,628 A | * | 3/1986 | Hickmann | 128/205.26 |
| 5,249,570 A | | 10/1993 | Cox | 128/206.28 |

* cited by examiner

Primary Examiner—John G. Weiss
Assistant Examiner—Teena Mitchell
(74) Attorney, Agent, or Firm—Workman, Nydegger & Seeley (57) ABSTRACT

An anesthesia mask for use with animals that comprises a body and a seal member. The body of the anesthesia mask is shaped to define a cavity therein that substantially conforms to the facial anatomy of an animal such as a dog. The body has a first end configured to interface with a breathing circuit and a second end that is open. The breathing circuit interface is located on the first end of the body so as to be substantially proximate to the nose of the animal when the nose portion is received in the cavity. The anesthesia mask includes a flexible and elastic seal member that is disposed across the second end of the body. In one embodiment, seal member is releasably engaged with the anesthesia mask. The seal member has an aperture formed therein through which a portion of the head of the animal is disposed so as to be removably received in the cavity. The seal member, because of its flexibility and elasticity, tends to resist deformation and thus substantially conforms to the anatomy of the animal when the anatomy is received in the cavity through the aperture formed in the seal member. The resilient seal member also facilitates ready placement of the anesthesia mask on the animal. In one embodiment, the anesthesia mask includes a self-sealing port through which instrumentation cables and the like may be passed into the cavity. The anesthesia mask also includes an optional external clip which can be used to capture and retain instrumentation cables exiting from the cavity.

28 Claims, 4 Drawing Sheets

ANESTHESIA MASK FOR ANIMALS

BACKGROUND OF THE INVENTION

1. The Field of the Invention

The present invention relates generally to anesthetic gas delivery devices. More particularly, embodiments of the present invention relate to an improved anesthesia mask for effective and reliable administration of anesthetic gases to animals.

2. The Prior State of the Art

It is generally acknowledged that administration of anesthetic to animals prior to and during surgery provides a variety of benefits, both to the animal and to the surgeon. In particular, the typical anesthetic sequence produces three desired results or effects in the animal. These three effects generally include: first, narcosis (animal is rendered unconscious); second, analgesia (the animal is rendered insensitive to pain) and suppression of reflexes; and third, muscle relaxation. Clearly, narcosis and analgesia provide a significant benefit to the animal since, as a result of these anesthetic effects, the animal suffers no pain and is unaware of the surgery taking place. Narcosis is important to the surgeon as well, since it allows the surgeon to further prepare the animal for surgery without harm to either the animal or the surgeon. Further, suppression of reflexes and muscle relaxation of the animal is important to the surgeon since it is obviously undesirable to have the animal's muscles and limbs flexing and/or moving while the surgeon is attempting to perform a surgical procedure.

Generally, the first effect, narcosis, is produced via intravenous administration of anesthetic. The effects of analgesia and reflex suppression are required in order to prepare the animal for intubation (i.e., placement of an endotracheal tube in the animal) and are typically achieved by using a temporary means to briefly force anesthetic gas into the animal's lungs and thereby place the animal in a deep state of unconsciousness. Upon achievement of analgesia and reflex suppression, the animal is then intubated for the remainder of the procedure. The final anesthetic effect of muscle relaxation is then achieved, and thereafter sustained, by connecting the endotracheal tube to a breathing circuit supplying the pressurized gaseous anesthetic.

While this anesthetic sequence is widely used and accepted, there are aspects of the associated equipment that remain problematic. One significant problem area concerns conventional masks used to introduce an anesthetic gas into the animal's lungs to achieve analgesia and reflex suppression. Intubation and the related equipment present another source of problems.

Turning first to the anesthesia masks, significant problems exist with conventional masks which have yet to be satisfactorily resolved. The major, overarching problem is that there is no known anesthesia mask that is specifically designed for use with animals, particularly dogs and other animals with muzzles or similar facial anatomy. As a necessary consequence, veterinarians have been forced to resort to a variety of incomplete and unsatisfactory solutions. Typically, veterinarians have taken one of two different approaches.

Some veterinarians simply use an anesthesia mask designed for humans. Obviously, a mask that fits a human well is clearly unsuited for use with canine anatomy. Accordingly, it is difficult, if not impossible, to adequately seal a human anesthesia mask around the muzzle of a dog. Further, because of the significant differences between canine and human anatomy, it is virtually impossible to encompass both the nose and mouth of a dog with an anesthesia mask designed for use by humans. Improperly shaped and sized anesthesia masks permit anesthetic to escape and thus it is difficult, if not impossible, for the anesthetist to determine if the proper volume of anesthetic is being delivered to the animal at the proper rate. This is clearly problematic because an improperly or inadequately anesthetized animal may compromise the surgeon's ability to perform the procedure. Likewise, the animal could suffer injury and possibly death if it is not properly anesthetized.

In an attempt to overcome the problems attending inadequately shaped and fitted anesthesia masks, anesthetists typically hold the mask in place in order to ensure the adequate flow and effective delivery of anesthetic that are required to induce a deep sleep in the animal. Generally, anesthetists are able to use this method effectively for only about ten minutes. Thus, surgical procedures lasting longer than ten minutes typically require intubation of the animal. As discussed in greater detail below, intubation introduces an additional set of problems, not the least of which are the logistics and expense involved with intubation.

Other veterinarians have moved a step further and attempted, with limited success, to modify human anesthesia masks to accommodate canine anatomy. While these modified anesthesia masks arguably represent an improvement over unmodified ones, problems remain. First, both time and expense are incurred in modifying human anesthesia masks to fit animals. Further, the functionality achieved by such modifications is modest at best. The surgeon or assistant may still have to hold the mask in place in order that the desired anesthetic effect can be achieved. Finally, the modified anesthesia mask is typically only suited for use with animals of the same size and anatomy as the one for which the mask was originally modified. Thus, while the modified mask may be somewhat effective for the particular animal for which it was modified, it is typically of limited utility where other animals are concerned.

In addition to modifying human anesthesia masks for use with animals, veterinarians have been forced to employ a variety of other primitive and generally ineffective equipment. Some of the other types of equipment currently in use by veterinarians include modified plastic containers, and anesthesia chambers constructed from modified fish tanks.

Another problem with conventional masks is that the animal's mouth needs to be allowed to open so that the tongue can move to prevent the animal from choking. At least one other problem with known masks is that they are typically ill-suited to accommodate the instrumentation necessary to monitor the vital signs of the animal when the animal is in the deep sleep typical of the final step of the anesthetic sequence. This is problematic because vital sign feedback is critically important during the procedure. For example, one vital sign or parameter of particular interest is the oxygen content of the blood of the animal. Oxygen content monitoring, or oximetry, provides valuable feedback on the effectiveness of the anesthetic gas and provides early warnings of possible complications that may arise during the procedure. Finally, oxygen content monitoring provides direct measurement of the material condition of the respiratory system of the animal. One way of monitoring the vital signs of the animal is to attach a monitor to the tongue of the animal.

As suggested above, intubation is another problem area where anesthetizing animals is concerned. One of the difficulties with the use of endotracheal tubes concerns the resistance of the breathing circuit to which the animal is connected during surgery. It is generally acknowledged that friction between a flowing fluid (which broadly encompasses both liquids and gases) and the pipe or tube through which it moves, resists fluid flow and tends to decrease the velocity of the fluid as the fluid travels down the tube. It follows that the overall loss in velocity increases with the length of the tube. Further, it is well known that the volume of gas delivered through a tube of a given size is directly proportional to the velocity of the gas, so that a relatively lower velocity corresponds to a relatively lower gas delivery rate. In view of the foregoing discussion, it is clear that the addition of an endotracheal tube to the breathing circuit increases the resistance of the circuit and tends to diminish the rate at which anesthetic gas is delivered. Thus, an intubated animal has to work harder to breath than a non-intubated animal. This is particularly problematic in view of the fact that the animal already has a diminished breathing capacity due to the effects of the anesthetic.

There are other problems as well that are associated with the use of endotracheal tubes. These problems include, but are not necessarily limited to, complications such as tracheitis and laryngeal edema, accidental dislodgement of the tube, chemical tracheitis resulting from the disinfectants used for cleaning the tubes, and infections resulting from improperly sterilized tubes. Finally, intubation is time-consuming and expensive, thus it is desirable to minimize or eliminate the need for intubation to the maximum extent practicable.

Accordingly, what is needed is an improved anesthetic delivery device or mask for animals, and for canines in particular. Specifically, the anesthesia mask should have a shape well-adapted for use with animal anatomies and should be sufficiently large to permit the mouth of the animal to remain open slightly during the procedure to prevent the animal from choking as well as allowing instruments to be placed in and/or near the mouth and tongue of the animal. Further, the anesthesia mask should completely receive both the nose and mouth of the animal in the cavity, but should avoid contact with the eyes of the animal. Also, the anesthesia mask should provide for substantial sealing of the cavity when the nose and mouth of the animal is received in the cavity. Additionally, the mask should be self-adjusting so that a single mask will securely and reliably fit, without modification, a variety of different animal anatomies. Finally, the mask should be well-suited to cooperate with instrumentation for monitoring animal vital signs.

SUMMARY AND OBJECTS OF THE INVENTION

The present invention has been developed in response to the current state of the art, and in particular, in response to these and other problems and needs that have not been fully or completely solved by the anesthesia masks currently in use by veterinarians.

Thus, it is an overall object of the present invention to provide an anesthesia mask that is particularly useful, when used in conjunction with an anesthetic breathing circuit, for anesthetizing a variety of different animals.

It is a another object of the invention to provide an anesthesia mask that defines a cavity shape closely approximating the shape of the facial anatomy of an animal so as to ensure effective, adequate, and reliable delivery of anesthetic.

It is a related object of the invention to provide an anesthesia mask having a breathing circuit interface disposed substantially proximate to the nose of the animal, when received in the cavity, so as to effectuate efficient delivery of the anesthetic to the animal.

It is similarly a related object of the invention to provide an anesthesia mask suitably large to encompass the mouth of the animal, as well as the nose of the animal, so as to prevent escape of anesthetic gas from the mouth.

It is another object of the present invention to provide an anesthesia mask having a self-adjusting seal so as to securely hold and seal the mask, without modification, on a variety of different facial anatomies.

Yet another object of the present invention is to provide an anesthesia mask that can be quickly and easily put on an animal.

Finally, it is an object of the present invention to provide an anesthesia mask having one or more self-sealing ports through which instrumentation wires can be passed so as to permit monitoring of the vital signs of the animal without significantly compromising the seal of the anesthesia mask.

In summary, the foregoing and other objects, advantages and features are achieved with improved anesthesia mask for use in supplying anesthetic to a variety of different animal types. Embodiments of the present invention are particularly suitable for use as in conjunction with a pressurized-gas anesthetic breathing circuit.

In one embodiment, the body of the anesthesia mask defines a cavity that is substantially in the shape of an animal muzzle. The body of the anesthesia mask has a first end that is configured to interface with a breathing circuit and a second end that is open. The body of the anesthesia mask is cut away from the first end to the second end in an area extending between the nose of the animal and the back of the mouth of the animal so that the anesthesia mask encompasses both the nose and mouth of the animal and simultaneously permits ready placement of instrumentation on the tongue of the animal. In this embodiment, a resilient seal member is disposed across the open second end of the body of the anesthesia mask and is releasably engaged with the body of the anesthesia mask so as to permit ready removal and replacement of the resilient seal member. The resilient seal member has an aperture formed therein through which the nose and mouth of the animal are received into the cavity. When the nose and mouth of the animal are inserted into the cavity, the sides of the aperture are deflected and/or deformed to the extent necessary to permit ready entry. Once situated in the cavity, the nose and mouth of the animal are substantially sealed therein and securely held in place by the resilient seal member which, because of its resilient nature, substantially conforms to the shape of the nose and mouth of the animal.

These and other objects, features, and advantages of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are not therefore to be considered to be limiting of its scope, the invention and its presently understood best mode for making and using the same will be described and explained with additional specificity and detail through the use of the accompanying drawings in which.

DETAILED DESCRIPTION OF THE PREFERRED EMBODIMENTS

Reference will now be made to figures wherein like structures will be provided with like reference designations. It is to be understood that the drawings are diagrammatic and schematic representations of some of the possible embodiments of the invention, and are not to be construed as limiting the present invention in any way, nor are the drawings necessarily drawn to scale.

Figure 1:
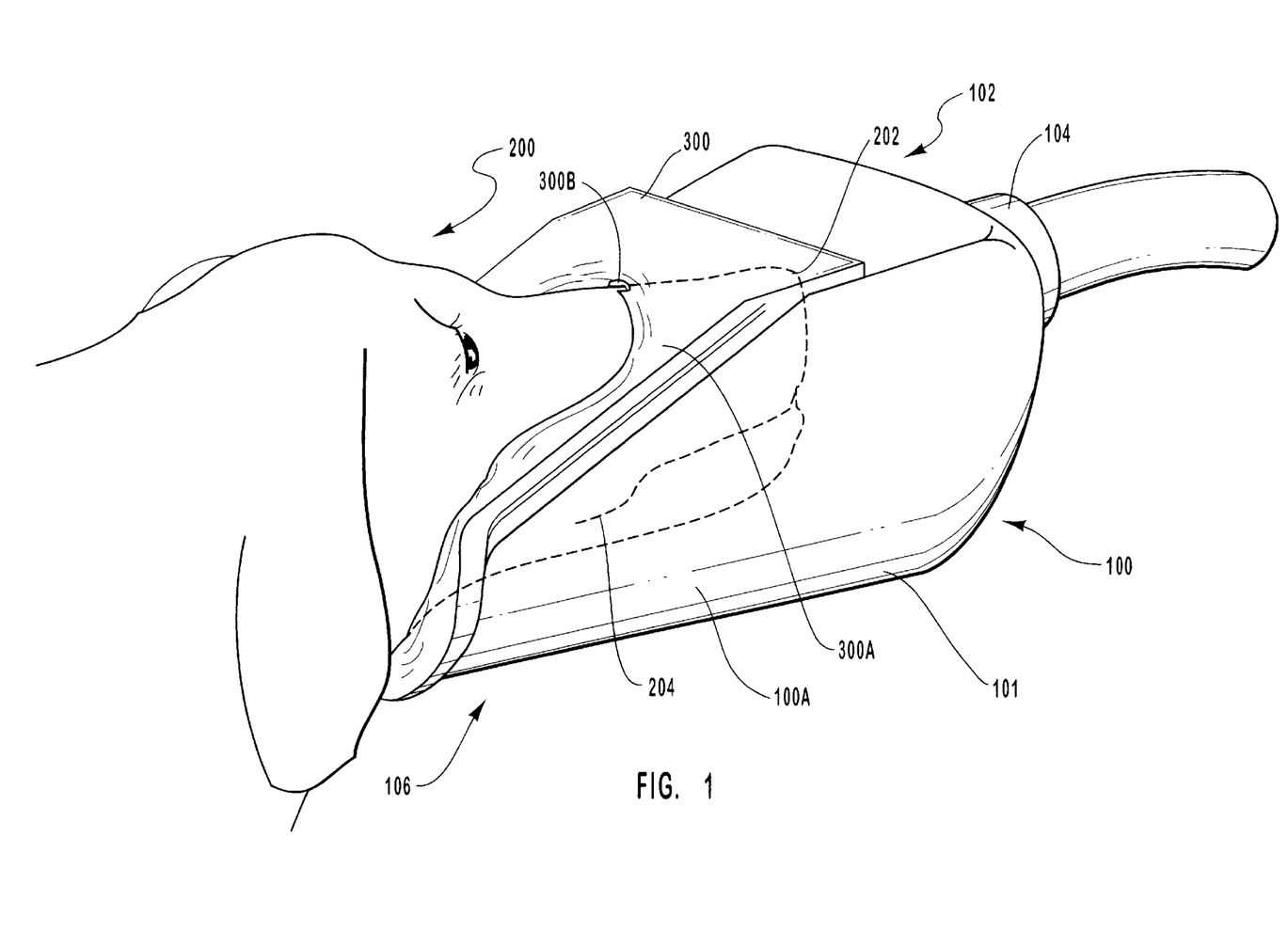
FIG. 1 is a perspective view of one embodiment of the inventive anesthesia mask with the muzzle of a dog disposed therein.

In general, the present invention relates to an anesthesia mask for use in anesthetizing animals preparatory to surgical procedures and the like. FIGS. 1 through 6 indicate various embodiments of the anesthesia mask conforming to the teachings of the invention. Reference is first made to FIG. 1, which depicts one embodiment of the inventive anesthesia mask, indicated generally as 100, secured to an animal generally indicated as 200. Anesthesia mask 100 comprises a body 101 and a seal member 300. As suggested in FIG. 2, one embodiment of body 101 defines a cavity 100A therein that is particularly suited to canines and the like. However, this invention contemplates as within its scope embodiments of body 101 suited for a variety of other animals, including but not limited to, rabbits, guinea pigs, cats, horses, lamas, mules, donkeys, livestock such as cows, sheep, and the like.

It is contemplated that a wide variety of materials for body 101 can be employed to achieve the functionality required by the present invention. In one embodiment, body 101 comprises a semi-rigid polymeric material or the like. In one embodiment, body 101 is lipid resistant and/or anesthesia gas non-permeable material or the like. The non-permeability of body 101 prevents body 101 from interfering with the concentration of the anesthesia gas by absorbing or reacting with the gas. Body 101 may be comprised of various light-weight materials such as polymer materials and various metals. In one embodiment, body 101 is transparent. Alternatively, body 101 may be translucent. Further, the transparency or translucence of body 101 permits visual monitoring of animal 200 during surgery. Body 101 should be semi-rigid so that the breathing of the animal does not cause body 101 to collapse.

Figure 2:
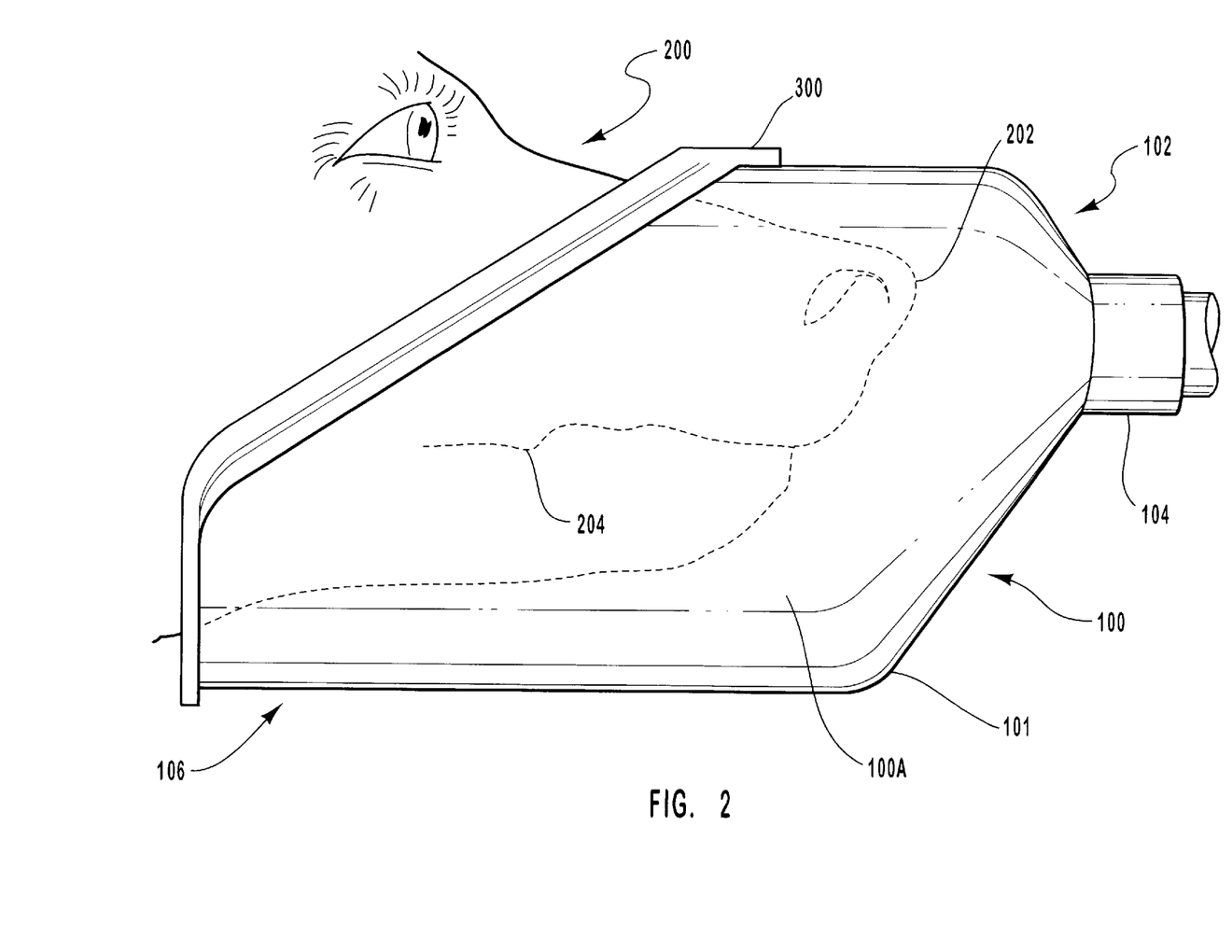
FIG. 2 is an elevation view of the structure of FIG. 1.

As indicated in FIGS. 1 and 2, body 101 of anesthesia mask has a first end 102 and a second end 106. First end 102 of body 101 includes a fitting 104 configured to interface with a breathing circuit (not shown). While fitting 104 is indicated as a substantially tubular shape, this invention contemplates as within its scope any size and shape of fitting 104 that would provide the functionality required by the present invention. In one embodiment, fitting 104 is located at first end 102 of body 101 so as to be substantially proximate to nose 202 of animal 200 and thereby optimize inhalation of anesthesia gases by animal 200 while simultaneously reducing rebreathing, by animal 200, of expelled gases. While fitting 104 is indicated in FIG. 2 as being located at first end 102 of body 101, this invention contemplates as within its scope fitting 104 being located at a variety of other locations and/or orientations on body 101, including but not limited to, the sides and/or bottom of body 101.

With continuing reference to FIGS. 1 and 2, second end 106 of body 101 is open, and, in one embodiment, is substantially cut away in a generally diagonal shape as indicated. The diagonal cutaway permits complete insertion and accommodation of both nose 202 and mouth 204 of animal 200 into body 101. Because body 101 has a shape, which substantially conforms to nose 202 and mouth 204 of animal 200, the amount of "dead" or unfilled, space in body 101 is minimized. In particular, body 101 is relatively deeper at first end 102 than at second end 106 so as to substantially conform to, respectively, nose 202 and mouth 204 of animal 200. The minimization of dead space achieved by this mask geometry increases the efficiency with which anesthetic can be delivered to animal 200 and thus reduces the level of effort required by animal 200 to breathe during the surgical procedure. Further, the cutaway geometry ensures that no more of the anatomy of animal 200 is enclosed by anesthesia mask 100 than is necessary. As a result, anesthesia mask 100 is relatively easy to place on animal 200 and also minimizes the discomfort of animal 200.

Figure 3:
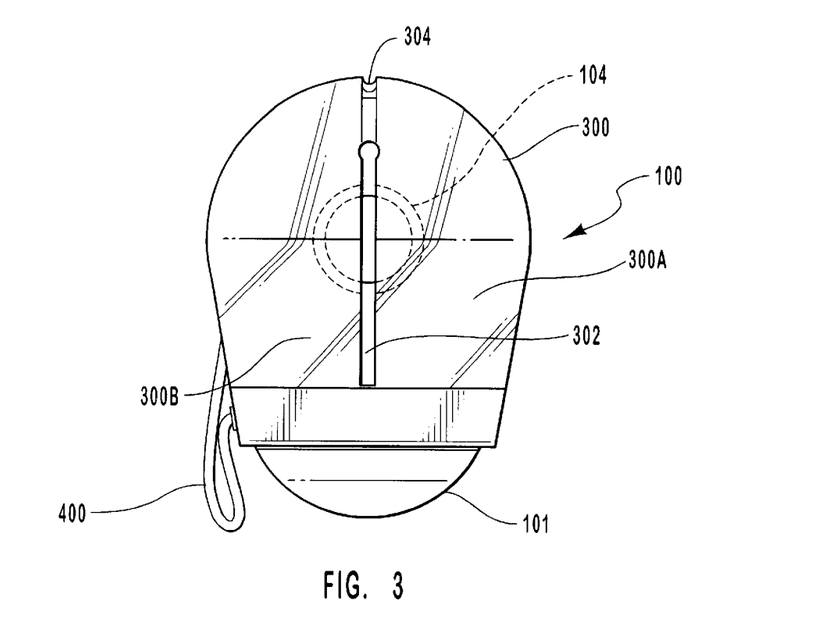
FIG. 3 is an end elevation view of an embodiment of the inventive anesthesia mask looking towards the opening in the seal member through which the muzzle of the animal is inserted.

As indicated in FIG. 3, body 101 preferably comprises a substantially oblong cross-section that is gradually tapered from top to bottom so as to substantially conform to the facial anatomy of a dog (not shown). However, it will be appreciated that the cross-sectional shape of body 101 may be infinitely varied as necessary to accommodate the facial structure and anatomy of a particular animal with which anesthesia mask 100 is desired to be used. Accordingly, the cross sectional shape of body 101 indicated in FIG. 3 simply represents one possible embodiment of the present invention and should not be construed to limit the scope thereof in any way.

Figure 4:
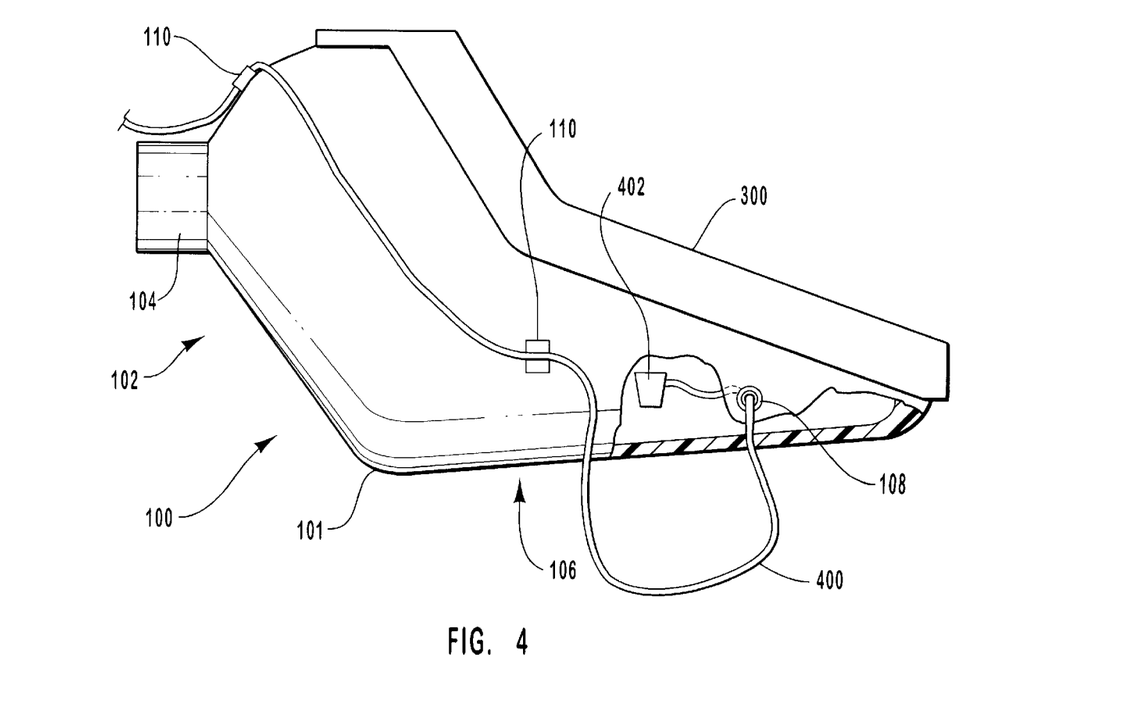
FIG. 4 is a partial breakaway elevation view of an embodiment of the inventive anesthesia mask depicting an instrument which can be used to monitor the animal's vital signs.

Seal member 300 is disposed across second end 106 of body 101 so as to substantially seal cavity 100A of body 101, as indicated in FIGS. 1, 3, and 4. Seal member 300 is one embodiment of a means for substantially sealing cavity 100A when a portion of the head of an animal (not shown) is removably received therein. Various other structures providing the functionality of seal member 300, as described herein, are contemplated as being within the scope of the present invention.

In one embodiment illustrated in the figures, seal member 300 is an integral one-piece member. Seal member 300 is composed of a flexible, resilient material such as rubber, a polymer material, or the like. In addition, seal member 300 may be composed of an anesthesia gas-impermeable polymer. Seal member 300 may also optionally be lipid-resistant. In one embodiment, seal member may be translucent or transparent. However, any material(s) or combination thereof that provides the functionality, described herein, of seal member 300 is contemplated as being within the scope of the present invention.

With reference now to FIG. 4, body 101 further includes one or more self-sealing ports 108 adapted to permit passage of instrumentation cables 400 or the like, so that instrumentation 402 can be connected to the animal (not shown) without seriously compromising the performance of anesthesia mask 100. It will be appreciated that self-sealing port 108 may be at various other locations in body 101 and perform the function thereof. In one embodiment, body 101 further includes a plurality of clips 110 or the like for use in capturing instrumentation cables 400 so as to prevent instrumentation cables 400 from interfering with the surgical procedure. Self-sealing port 108 may also be used to admit other components to cavity 100A including, but not limited to, wire-clip assemblies (not shown) for holding the tongue of animal 200 (not shown) in place during the procedure.

Figure 5:
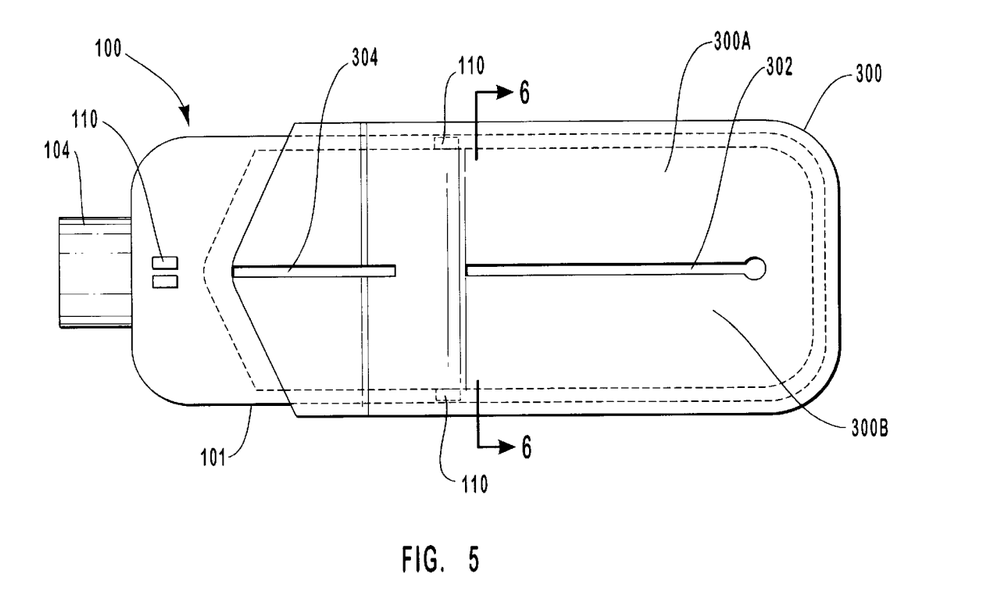
FIG. 5 is a plan view looking down towards the seal member of one embodiment of an inventive anesthesia mask.

As illustrated more particularly in FIG. 5, seal member 300 further comprises first seal portion 300A and second seal portion 300B. As previously mentioned, in one embodiment, first seal portion 300A and second seal portion 300B are integral with each other. Alternatively, first seal portion 300A and second seal portion 300B are separate members designed to cooperate together to substantially sealingly cover second end 106 of body 101. As indicated in FIG. 5, first seal portion 300A of seal member 300 cooperates with second seal portion 300B of seal member 300 to define an aperture 302. In one embodiment, aperture 302 is a slot. However, it will be appreciated that the shape, dimensions, and/or location of first seal portion 300A and second seal portion 300B may alone, or in various combinations, be varied so as to define a wide variety of apertures 302 as required to accommodate different sizes and types of animals. Accordingly, any and all of such modifications to first seal portion 300A and second seal portion 300B are contemplated as being within the scope of the present invention.

The inherently flexible and elastic nature of first seal portion 300A and second seal portion 300B has at least three important benefits. First, because they are flexible and resilient, first seal portion 300A and second seal portion 300B of seal member 300 can stretch and/or deform, as required, to define a virtually infinite number of aperture geometries so as, by way of example and not limitation, to permit anesthesia mask 100 to accommodate virtually any shape of anatomy, such as the dog shown in FIG. 1. Accordingly, anesthesia mask 100 is thus "standardized" so that it is well-suited for use with the facial anatomies of a wide variety of different animals. This feature of the present invention thus eliminates the need for veterinarians to stock numerous different anesthesia masks to accommodate the needs of the various animals that they treat. It will be appreciated, however, that the size differentiation between various species may require different sized anesthesia masks. It is contemplated that the present mask, although the size may be changed, can be used for a wide variety of animals including but not limited to dogs, cats, horses, donkeys, mules, lamas, livestock, rabbits, guinea pigs, and the like.

Another important benefit that flows from the inherently flexible and elastic nature of first seal portion 300A and second seal portion 300B of seal member 300 is that those portions naturally and continually resist the deformation imposed by the anatomy of the animal and thus stretch and/or deform only to the extent necessary to accommodate the anatomy of the animal. That is, first seal portion 300A and second seal portion 300B act to substantially seal cavity 100A by exerting a small but continuous force on the anatomy of animal 200, as indicated in FIG. 1, both during placement of anesthesia mask 100, and after anesthesia mask 100 has been completely positioned. Further, the force collectively exerted by first seal portion 300A and second seal portion 300B of seal member 300 helps to ensure that anesthesia mask 100 remains securely in place on animal 200 during the surgical procedure. In an alternative embodiment, seal member 300 is supplemented with one or more straps, or the like to hold that anesthesia mask 100 securely in place on animal 200.

Figure 6:
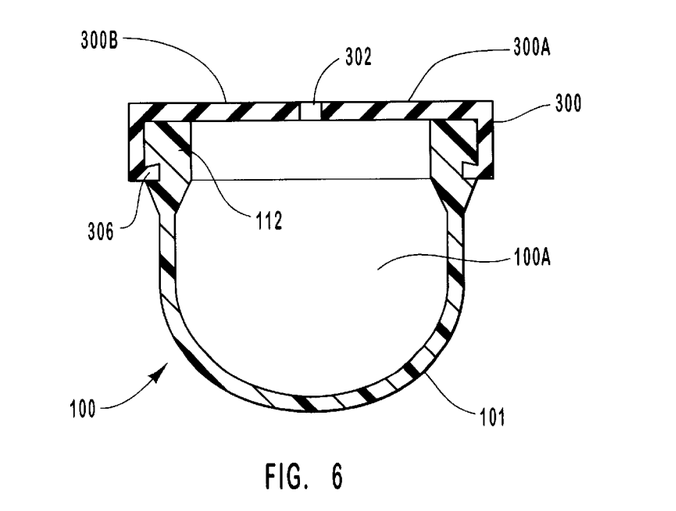
FIG. 6 is a cross-sectional elevation view taken through the structure of FIG. 5 along line 6—6.

Note that the force exerted by first seal portion 300A and second seal portion 300B of seal member 300 may be adjusted by selecting seal member 300 materials of relatively greater, or lesser, thickness (see FIG. 6). Thus, a relatively thicker seal member would exert a relatively greater force, and a relatively thinner seal member 300 would exert a relatively lesser force as aperture is enlarged by the anatomy of animal 200.

The flexible and resilient nature of first seal portion 300A and second seal portion 300B of seal member 300 has at least one other important benefit. Because their respective shapes are readily modified, first seal portion 300A and second seal portion 300B of seal member 300 permit anesthesia mask 100 to be quickly and easily placed on the animal. This feature makes anesthesia mask 100 convenient for the veterinarian to use and provides a level of comfort for the animal on which it is placed.

In one embodiment of seal member 300, as illustrated in FIG. 5, has an optional channel 304 which is configured to capture instrumentation cables (FIG. 4) or the like. Channel 304 cooperates with clips 110, depicted in FIG. 4, to keep instrumentation cables 400 from interfering with the surgical procedure or getting inadvertently caught or tangled with another object.

As indicated in FIG. 6, seal member 300 and body 101 each comprise mating structure, 306 and 112, respectively, disposed around the respective perimeters of seal member 300 and body 101. Mating structure 306 and 112 are well-adapted to permit seal member 300 to substantially seal cavity 100A and yet be releasably engaged with anesthetic mask 100. Note that mating structure 306 and 112 represent only one possible embodiment of structure adapted to suit the purpose described and should not be construed to limit the scope of the present invention in any way. Further, this invention contemplates as within its scope any structure that would provide the described functionality.

Finally, in an alternative embodiment (not shown), seal member 300 is disposed across second end 106 of a substantially cylindrical body 101. In this embodiment, seal member 300 terminates in a circumferential elastic band that defines an aperture 302. The circumferential elastic band performs the same functions, described herein, as first seal portion 300A and second seal portion 300B of seal member 300.

By way of summary, and with reference to the various figures, anesthesia mask 100 is oriented generally as indicated in FIG. 3 (as viewed from the perspective of the animal (not shown)) and is slidingly placed about the nose 202 and mouth 204 of animal 200 so as to assume the disposition indicated in FIG. 1. As anesthesia mask 100 is placed on animal 200, first seal portion 300A and second seal portion 300B stretch, and deflect in response to insertion of nose 202 and mouth 204 of animal 200, as indicated in FIG. 1. That is, the shapes of first seal portion 300A and second seal portion 300B are modified in response to placement of anesthesia mask 100 on animal 200, so that those portions define an aperture 302 that substantially conforms to the shape of the nose 202 and mouth 204 of animal 200 (FIG. 1) on which anesthesia mask 100 is placed. Once in place, first end 104 of body 101 of anesthesia mask 100 is connected to a breathing circuit (not shown).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. An anesthesia mask for animals, comprising:
   (a) a body defining a cavity therein, said body having a first end configured to interface with a breathing circuit and second end; and
   (b) a seal member disposed across said second end of said body, said sealing member having an aperture formed therein of variable size through which a portion of the head of an animal can be inserted such that the animal's nose and mouth are received in said cavity while the animal's eyes remain outside said cavity, said seal member substantially conforming to the portion of the head so as to substantially seal said cavity when the portion of the head is received therein.

2. An anesthesia mask as recited in claim 1, wherein said cavity defined by said body has a shape substantially corresponding to the portion of the head of an animal.

3. An anesthesia mask as recited in claim 1, wherein said cavity has a substantially cylindrical shape.

4. An anesthesia mask as recited in claim 1, wherein said first end of said body is proximate to the portion of the head when the portion is received in said cavity so as to facilitate efficient transmission of anesthesia gas to said animal.

5. An anesthesia mask as recited in claim 1, wherein said body comprises a cut away portion extending from said second end toward said first end, said cut away portion being configured to facilitate ready placement and removal of said anesthesia mask.

6. An anesthesia mask as recited in claim 1, wherein said body is translucent.

7. An anesthesia mask as recited in claim 1, wherein said body is transparent.

8. An anesthesia mask as recited in claim 1, wherein said seal member is releasably engaged with said body.

9. An anesthesia mask as recited in claim 1, wherein said seal member is translucent.

10. An anesthesia mask as recited in claim 1, further comprising at least one strap to assist in securely retaining said anesthesia mask on the animal.

11. An anesthesia mask as recited in claim 10, wherein said seal member and said body are configured to be connected to each other so that said seal member is releasably engaged with said body.

12. An anesthesia mask as in claim 1, wherein said seal member is substantially composed of material selected from a group consisting of a polymer material and rubber.

13. An anesthesia mask for animals, comprising:
   (a) a body defining a cavity therein, said body having a first end configured to interface with a breathing circuit and an open second end; and
   (b) a resilient seal member disposed across said second end of said body, said seal member having an aperture formed therein through which a portion of the head of an animal can be placed such that the animal's nose and mouth are received in said cavity while the animals eyes remain outside said cavity, said resilient seal member substantially conforming to the portion of the head so as to substantially seal said cavity when the portion of the head is received therein.

14. An anesthesia mask as recited in claim 13, wherein said cavity of said body has a shaped substantially corresponding to the portion of the head of an animal.

15. An anesthesia mask as recited in claim 14, further comprising a clip mounted on said body, said clip being configured to removably retain instrumentation cable.

16. An anesthesia mask as recited in claim 13, wherein said second end of said body is at least partially cut away.

17. An anesthesia mask as recited in claim 13, wherein said body is anesthesia gas-impermeable.

18. An anesthesia mask for animals, comprising:
   (a) a body defining a cavity therein configured to substantially correspond to the shape of the muzzle of an animal, said body having a first end configured to interface with a breathing circuit and an open second end, said second end of said body being at least partially cut away; and
   (b) a resilient seal member disposed across said second end of said body, said seal member being releasably engaged with said body, said seal member having an aperture formed therein through which at least a portion of the muzzle of the animal is received in said cavity, said resilient seal member substantially conforming to the portion of the muzzle so as to substantially seal said cavity when the portion of the muzzle is received therein.

19. An anesthesia mask as recited in claim 18, wherein said body further comprises at least one self-sealing port configured to accommodate passage of at least one instrumentation cable into said cavity.

20. An anesthesia mask as recited in claim 16, wherein said instrumentation cable is attached to oximetry instrumentation.

21. An anesthesia mask as recited in claim 18, wherein said resilient seal member is substantially composed of a polymer material.

22. An anesthesia mask as recited claim 18, wherein said body is composed of a polymer material.

23. An anesthesia mask for animals, comprising:
   (a) a body defining a cavity therein, said body having a first end configured to interface with a breathing circuit and a substantially open second end; and
   (b) means for substantially sealing said cavity, said means for substantially sealing said cavity having an aperture formed therein capable of receiving a portion of an animal including at least the animal's mouth and nose but not the eyes, said means for substantially sealing said cavity being self-adjusting to substantially conform to various configurations of the portion of the animal disposed therethrough.

24. An anesthesia mask for animals as recited in claim 23, wherein said cavity has a shape substantially corresponding to the portion of the head of an animal.

25. An anesthesia mask for animals as recited in claim 23, wherein said means for substantially sealing said cavity is releasably engaged with said body.

26. An anesthesia mask for animals as recited in claim 23, wherein said means for substantially sealing said cavity comprises a seal member.

27. An anesthesia mask for animals as recited in claim 26, wherein said seal member is disposed across said second end of said body, said seal member releasably engaging said body.

28. An anesthesia mask for animals, comprising:
   (a) a body defining a cavity therein, said body having a first end configured to interface with a breathing circuit and a substantially open second end;
   (b) a resilient seal member disposed across said second end of said body, said seal member having an aperture formed therein through which a portion of the head of an animal can be placed such that the animal's nose and mouth are received in said cavity while the animals eyes remain outside said cavity, said resilient seal member substantially conforming to the portion of the head so as to substantially seal said cavity when the portion of the head is received therein; and
   (c) a self-sealing port configured to accommodate passage of instrumentation cable into said cavity.

* * * * *

UNITED STATES PATENT AND TRADEMARK OFFICE
CERTIFICATE OF CORRECTION

PATENT NO.    : 6,349,725 B1
DATED         : February 26, 2002
INVENTOR(S)   : D.H. Perkins, Ray H. Perkins and Ryan C. Perkins It is certified that error appears in the above-identified patent and that said Letters Patent is hereby corrected as shown below:

Column 10,
Line 39, after "claim" change "16" to -- 23 --

Signed and Sealed this

Eleventh Day of May, 2004

JON W. DUDAS
*Acting Director of the United States Patent and Trademark Office*